(12) United States Patent
Hagen et al.

(10) Patent No.: US 8,957,229 B2
(45) Date of Patent: Feb. 17, 2015

(54) METHOD FOR THE PRODUCTION OF A MIXTURE OF LACTIDE DERIVATIVES

(75) Inventors: Rainer Hagen, Berlin (DE); Adam B. Verweij, Aduard (NL); Udo Muhlbauer, Berlin (DE); Joachim Schulze, Soest (DE); Wolfgang Tietz, Biendorf (DE); Klaus-Dieter Göhler, Grimma (DE); Olga Renate Göhler, legal representative, Grimma (DE)

(73) Assignees: Uhde Inventa-Fischer GmbH, Berlin (DE); Uhde GmbH, Dortmund (DE)

( * ) Notice: Subject to any disclaimer, the term of this patent is extended or adjusted under 35 U.S.C. 154(b) by 17 days.

(21) Appl. No.: 13/060,553

(22) PCT Filed: Aug. 28, 2009

(86) PCT No.: PCT/EP2009/006252
§ 371 (c)(1),
(2), (4) Date: Jan. 13, 2012

(87) PCT Pub. No.: WO2010/022966
PCT Pub. Date: Mar. 4, 2010

(65) Prior Publication Data
US 2012/0149920 A1    Jun. 14, 2012

(30) Foreign Application Priority Data

Aug. 29, 2008 (DE) .......................... 10 2008 044 947

(51) Int. Cl.
*C07D 319/00* (2006.01)
*C07D 319/12* (2006.01)
*C07B 55/00* (2006.01)

(52) U.S. Cl.
CPC ............ *C07D 319/12* (2013.01); *C07B 55/00* (2013.01)
USPC ...................................................... 549/274

(58) Field of Classification Search
USPC ...................................................... 549/274
See application file for complete search history.

(56) References Cited

U.S. PATENT DOCUMENTS

| | | | |
|---|---|---|---|
| 5,091,544 A * | 2/1992 | Bhatia ............................ | 549/274 |
| 5,319,107 A * | 6/1994 | Benecke et al. ............... | 549/274 |
| 5,463,086 A * | 10/1995 | Kubota et al. ................ | 549/274 |
| 5,801,255 A | 9/1998 | Ohara et al. | |
| 6,277,951 B1 * | 8/2001 | Gruber et al. ................ | 528/354 |
| 2006/0014975 A1 | 1/2006 | Coszach et al. | |
| 2006/0036062 A1 * | 2/2006 | Ramakrishna et al. ....... | 528/354 |

FOREIGN PATENT DOCUMENTS

| | | | | |
|---|---|---|---|---|
| DE | 4230951 A1 | 3/1994 | | |
| DE | 4407036 A1 * | 9/1995 | ........... | C07D 319/12 |
| DE | 19902879 A1 | 8/2000 | | |
| EP | 0 657 447 A * | 12/1994 | ........... | C07D 319/12 |
| EP | 0657447 A | 6/1995 | | |
| EP | 1577346 A1 | 9/2005 | | |
| WO | WO8404311 A1 | 11/1984 | | |
| WO | 8810260 A | 12/1988 | | |
| WO | 2005056509 A1 | 6/2005 | | |

OTHER PUBLICATIONS

Tsukegi et al., Polym. Degradation and Stability 92 (2007) 552-559.*
Tsukegi et al., Polym. Degradation and Stability 92 (2007) 552.*
Motoyama et al. Polym Degrad Stab 92 (2007), 1350.*
Fan et al. Polym Degrad Stab 80 (2003), 503.*
Sterzel (Machine translation) Ger.Offen. (1995), DE 4407036 A1 Sep. 7, 1995.*
Ovitt et al., "Stereochemistry of Lactide Polymerization with Chiral Catalysts: New Opportunities for Stereocontrol Using Polymer Exchange Mechanisms," JACS Articles 2002, 124(7):1316-1326, published on the Web Jan. 26, 2002.
Ovitt et al., "Stereoselective Ring-Opening Polymerization of *meso*-Lactide: Synthesis of Syndiotactic Poly(lactic acid)," JACS 1999, 121(16):4072-4073.
Radano et al., "Stereoselective Polymerization of a Racemic Monomer with a Racemic Catalyst: Direct Preparation of the Polylactic Acid Stereocomplex from Racemic Lactide," JACS 2000, 122(7):1552-1553, published on the Web Feb. 5, 2000.
Spassky et al., "Highly stereoelective polymerization of *rac*-(D,L)-lactide with a chiral Schiff's base/aluminium alkoxide initiator," Macromol. Chem. Phys. 1996, 197:2627-2637.
International Search Report, Application No. PCT/EP2009/006252, mailed Feb. 15, 2010.
International Preliminary Report on Patentability issued in PCT/EP2009/006252, completed on Nov. 26, 2010, 22 pages (English translation).

* cited by examiner

*Primary Examiner* — Nizal Chandrakumar
(74) *Attorney, Agent, or Firm* — Faegre Baker Daniels LLP (57) ABSTRACT

A mixture of cyclic diesters derived from lactic acid and in cases a mixture of a racemate of dilactide may be produced in several different processes. In some instances, the process can thereby start from the corresponding alpha-hydroxycarboxylic acids, the corresponding cyclic diesters or oligomers of the corresponding alpha-hydroxycarboxylic acids.

22 Claims, 1 Drawing Sheet

METHOD FOR THE PRODUCTION OF A MIXTURE OF LACTIDE DERIVATIVES

CROSS-REFERENCE TO RELATED APPLICATIONS

The present application is a national phase application of PCT Application No. PCT/EP2009/006252 filed pursuant to 35 U.S.C. §371, which claims priority to DE 10 2008 044 947.4 filed Aug. 29, 2008. Both applications are incorporated by reference herein in their entirety.

TECHNICAL FIELD

The present invention relates to three variants for producing a mixture of cyclic diesters derived from lactic acid and in particular of a racemate of dilactide. In some embodiments, the process can start from the corresponding α-hydroxycarboxylic acids, the corresponding cyclic diesters or oligomers of the corresponding α-hydroxycarboxylic acids. All 3 variants of the method have in common a racemisation of the chiral carbon atom of the educts.

BACKGROUND

Polylactic acid is a promising biopolymer having a low thermostability. Were it possible to achieve better thermal properties, the possible applications would increase greatly.

In order to be able to produce PLLA with optimal thermal properties, (optically) very pure L-lactide (L-LA) is required. Currently, the most used method for producing L-lactide includes a two-stage polycondensation of lactic acid to form an oligomer followed by a depolymerization. Because of the prevailing high temperatures, which are required for a rapid reaction course, and also because of cationic impurities of the lactic acid or of the reaction vessels (e.g. by corrosion), racemisation can occur, as a result of which meso-lactide is produced as by-product. This product must be separated from the main product since meso-lactide (M-LA) has a negative effect on the properties of the polymer produced during the polymerization of L-lactide. The result thereby is a notable reduction in the melting temperature and also in the glass transition temperature as shown in Table 1 below, while the mechanical properties likewise change.

TABLE 1

|  | PLLA | PRLA | PMLA (a/s) | sc-PLA | sbc-PLA |
|---|---|---|---|---|---|
| Tg ° C. | 55-60 | 50-55 | 40-45/34 | 80-90 | 50-55 |
| Tm ° C. | 140-170 | — | —/153 | 210-230 | 185-195 |

Tg: glass transition temperature
Tm: melting point
PLLA: L-polylactic acid
PRLA: racemic polylactic acid
PMLA: meso-polylactic acid
a: amorphous
s: syndiotactic
sc: stereocomplex
sbc: stereoblock copolymer Meso-lactide, like L-lactide, is a cyclic diester with two optically active carbon atoms in the ring. It has an optical R- and an S-center and is therefore optically inactive. The polymerization of meso-lactide leads to an amorphous polymer. A syndiotactic polymer can be produced using a stereoselective catalyst (Tina M. Quitt and Geoffrey W. Coates, J. Am. Chem. Soc. 1999, 121, 4072-4073), the thermal properties of which are however poorer than those of PLLA.

Stereocomplexes of polylactic acid (PLA) can resolve the problem of low thermal stability but the optical counterpart of L-polylactic acid (PLLA) is required for the production of stereocomplexes. D-polylactic acid (PDLA) is available only in small quantities and is very expensive.

Rac-lactide has been obtained to date from equal quantities of D,D- and L,L-lactide by melting. Since D,D-lactide is relatively expensive because of the great complexity for producing D-lactic acid, reuse as a monomer for the polylactic acid production has to date been more of theoretical interest. The properties of D,D-L,L-stereopolymers are thereby of great interest since they have significantly better thermostabilities and hence could eliminate one of the disadvantages of polylactic acid.

Dilactides that are composed of the enantiomers of lactic acid are already known. WO 1984/04311 A1 describes a method for the production of a polymer from caprolactone and lactide that is used for the production of everyday objects in medicine and care technology. The dilactide is commercially available and is predominantly composed of the two enantiomers of lactic acid, L-(−)- and D-(+)-lactic acid. This mixture is frequently associated with dilactide and includes the same enantiomers of lactic acid, namely D-lactic acid or L-lactic acid. No allusion to the production of these dilactides composed of the same enantiomers is given.

The polymerization of a mixture of meso-lactide and L-lactide leads to a copolymer, the thermal properties of which are inferior to those of PLLA. Meso-lactide can also be used in the production of racemic lactic acid (D/L-LA) by hydrolysis with water. However, these applications are only of subordinate interest from a commercial point of view so that an increase in the economic value is sought.

SUMMARY

In some embodiments, the present invention is directed to a method that enables the production of a mixture of the cyclic diesters of the general Formulae Ia, Ib and/or Ic

In some embodiments, a mixture of the cyclic diesters of the general Formula Ia, Ib and Ic can be produced from one of:

a) an α-hydroxycarboxylic acid of Formula IIa and/or IIb b) a substantially or completely stereoisomer-pure compound of Formula Ia, Ib or Ic or a mixture of two or three of the compounds, or c) an oligomeric or polymeric hydroxycarboxylic acid of the general Formula III wherein respectively in the compounds of Formulae I, II and III, R stands for a linear or branched aliphatic alkyl radical with 1 to 6 C-atoms and n=1 to 50 is meant in Formula III. The starting material is converted with a catalyst or a mixture of at least two catalysts.

In some embodiments, an equimolar mixture of the two enantiomers of the dilactide of lactic acid, D,D-dilactide and L,L-dilactide can be produced via the following steps:
a) (−)-form L-(−)-lactic acid is converted with trioctylamine into trioctyl ammonium lactate,
b) the trioctyl ammonium lactate is distilled in the presence of a catalyst, a fraction being obtained which is composed essentially of the two enantiomers of the dilactide of lactic acid, D,D-dilactide and L,L-dilactide and can still contain D,L-lactide, and
c) the above-mentioned fraction is mixed with acetone and hence recrystallized to obtain colorless crystals having a melting point of 112 to 119° C. The colorless crystals are composed substantially equimolarly or equimolarly of D,D-dilactide and L,L-dilactide.

In some embodiments, a mixture of the cyclic diesters can be used to produce amorphous polylactides. In some embodiments, the mixture can be used to produce stereocomplex polylactice acid and/or stereoblock copolymers of lactic acid.

DETAILED DESCRIPTION

In some embodiments, a mixture of the compounds of Formulae Ia, Ib and/or Ic (below) can be produced:

In some embodiments, an α-hydroxycarboxylic acid of Formula IIa and/or IIb (respectively in the compounds of Formulae I and II, R standing for a linear or branched aliphatic alkyl radical with 1 to 6 C-atoms) is converted with a catalyst or a mixture of at least two catalysts.

In some embodiments, the production of the mixture of compounds Ia, Ib and/or Ic, starts from an α-hydroxycarboxylic acid of Formulae IIa and/or IIb that is converted in the presence of a plurality of catalysts. Both respectively the compounds IIa and IIb can thereby be used as substantially or completely enantiomer-pure compounds, the process can also start however from a mixture of the two enantiomer-pure compounds in any stoichiometric ratio. There is understood by "substantially enantiomer-pure" a mixture of compounds IIa and IIb with an enantiomer excess (ee) of more than 99% ee.

In some embodiments, production of the above-mentioned mixture of compounds Ia, Ib and/or Ic, a substantially or completely stereoisomer-pure compound of Formulae Ia, Ib or Ic or also mixtures of Ia, Ib and Ic is converted with a catalyst or a mixture of at least two catalysts. There is thereby understood by "substantially stereoisomer-pure" the mixture of compounds Ia, Ib and/or Ic, in which one of the mentioned compounds is present in an excess with respect to the sum of the two other compounds of at least 99%. In this embodiment, the process starts with a single compound of Formulae Ia, Ib or Ic, a conversion of the stereocenters of the cyclic diesters that are used taking place in the course of the process. If the process starts with a mixture of compounds Ia, Ib and/or Ic, a mixture of these compounds is obtained again but with a changed composition.

In some embodiments, the mixture of compounds Ia, Ib and/or Ic, can be produced by converting with a catalyst or a mixture of at least two catalysts an oligomeric or polymeric hydroxycarboxylic acid of the general Formula III (n=1 to 50 being meant in Formula III).

In some embodiments, an oligomeric or polymeric hydroxycarboxylic acid of Formula III is depolymerized. In some embodiments, all possible stereoisomers can be used for the hydroxycarboxylic acid of Formula III. This is indicated in Formula III by the tortuous bond of the radical R. The absolute configuration of the respective stereocenter (R or S) is thereby irrelevant.

In some embodiments, the catalyst can be chosen for all of the three above-mentioned variants of the method according to the invention from the group consisting of metal compounds of groups 1 to 14 of the periodic table. In some embodiments, the catalyst may be a metallic salt, an organometallic compound, an alkoxide, an oxide or a salt of an organic acid. In some embodiments, the catalyst may be metallic salts and/or organometallic compounds of Na, K, Mg, Ca, Fe, Ti, Zn, Sn or Sb. In some embodiments, the catalyst may be oxides, hydroxides, carbonates, benzoates, lactates or octoates of Na, K, Mg, Ca, Fe, Ti, Zn, Sn or Sb. In some embodiments, the catalyst may be MgO, CaO, $K_2CO_3$, sodium lactate, potassium benzoate, tin octoate $SnOc_2$, dibutyltin oxide $Bu_2SnO$, $BuSnOc_3$ or SnO.

In some embodiments, the catalyst may be nitrogen-containing or phosphorus-containing organic compounds. In some embodiments, the catalyst is a primary, secondary and/or tertiary amine and/or an aliphatic, aromatic N-heterocyclic compound with 5-7 ring atoms or a phosphines. In some embodiments, the catalyst may be a primary, secondary and/or tertiary amine with 1 to 20 C-atoms. In some embodiments, the catalyst may be triethylamine, ethyldiisopropylamine, dibutylamine, tributylamine, trioctylamine, dicyclohexylamine, 4-(N,N-dimethyl)-aminopyridine, 2,2,6,6-tetramethylpiperidine, 1,2,2,6,6-pentamethylpiperidine and/or tributylphosphine.

In some embodiments, the catalysts may be considered as being polymerization catalysts, racemization catalysts or stereoselective catalysts.

Polymerization Catalysts

A large number of compounds are known as polymerization catalysts for PLA. They are frequently metallic- or organometallic salts, such as alkoxides, oxides, salts of organic acids etc. Tin octoate is most often used. Furthermore, also other tin compounds, such as e.g. butyl tin octoate, dibutyl tin oxide, SnO or also tin are used. Also the use of compounds of Ti, Fe, Zn, Sb etc. is possible.

Racemization Catalysts

Racemization catalysts that are used for the racemization of lactides should be weakly alkaline compounds and effect no ring-opening polymerisation (ROP). There are three compound classes of racemization catalysts:

a) Group 1a and 2a metal oxides, carbonates, hydroxides or salts of organic acids, such as e.g. sodium lactate, potassium benzoate, $K_2CO_3$, MgO, CaO etc.

b) Amines, primary, secondary or tertiary amines with a boiling or melting point which is high enough that the compound remains in the reaction. Examples include secondary or tertiary amines, such as e.g. triethylamine (TEA), tributylamine (TBA), trioctylamine (TOA), dibutylamine (DBA), di-cyclohexylamine (DCHA), dimethylaminopyridine (DMAP) etc.

c) Primary, secondary or tertiary phosphines.

For all the volatile catalysts mentioned here, it applies that the boiling point must be high enough that the compound remains in the reaction.

In some embodiments, in selecting a racemization catalyst, care must be taken that the catalyst catalyzes only a racemization and no ring-opening of the lactide. These two conflicting reactions depend upon the chemical and steric structure of the catalyst. A ring-opening makes the separation of a lactide mixture after the racemization more difficult and lowers the yield. The purity of the racemic lactide mixture after the separation is important for a stereoselective catalysis for producing sc-PLA and sbc-PLA.

In some embodiments, secondary and tertiary amines and phosphines are selected as catalysts because of steric hindrance of the active center. In some embodiments, the catalysts are voluminous organic radicals, such as e.g. the cyclohexyl group in DCHA.

The ring-opening is hindered by them and their weak alkaline activity is sufficient for the racemization. However, it applies for all the mentioned catalysts that they lose their selectivity with high temperatures or long reaction times.

Stereoselective Catalysts

Stereoselective catalysts (Spassky et al., Macromol. Chem. Phys. (1996), 197, 2672; Ovitt and Coates, J. Am. Chem. Soc., (2002), 124, 1316; Radano and Baker, J. Am. Chem. Soc., (2000), 122, 1552) are very specific polymerization catalysts that have a chiral center. They catalyze exclusively the polymerization reaction of specific isomers. Different types are differentiated here. One class of these catalysts can catalyze only the reaction of the isomer (L,L/D,D-lactide+ ssc→PLLA+D,D-lactide), whereas another type with two active centers can polymerize two isomers at the same time (L,L/D,D-lactide+ssc→PLLA+PDLA=sc-PLA). Catalysts are also known which can polymerize L- or D-lactide alternately (L,L/D,D-lactide+ssc→(PLLA-co-PDLA)$_n$=sbc-PLA).

Furthermore, in some embodiments, it is advantageous respectively with the above-mentioned variants of the method according to the invention if the catalyst, with respect to the respective educts of the different variants, i.e. the α-hydroxycarboxylic acid of Formula IIa and/or IIb, of substantially stereoisomer-pure or stereoisomer-pure compound of Formula Ia, Ib or Ic or a mixture of two or three of the compounds, or of the oligomeric or polymeric hydroxycarboxylic acid of the general Formula III, is used in a weight ratio between 1:1 and 1:10,000. In some embodiments, the weight ratio is between 1:10 and 1:5,000. In some embodiments, the weight ratio is between 1:100 and 1:1,000.

Surprisingly, it was able to be established that in some embodiments, the molar ratio of the compounds of Formula Ia and Ib, obtained in the method, is between 1:2 and 2:1. In some embodiments, the molar ratio is between 1:1.2 and 1.2:1. In some embodiments, the molar ratio is about 1:1.

Furthermore, it was found surprisingly that in some embodiments, the molar ratio of the sum of the compounds of Formula Ia and Ib, obtained in the method, to the compound of Formula Ic (Ia+Ib)/Ic is between 10:1 and 1:1. In some embodiments, the molar ratio of the sum is between 10:1 and 2:1.

In some embodiments, the conversion is implemented at temperatures between 80 and 300° C. In some embodiments, the conversion takes place between 100 and 200° C. In some embodiments, the conversion takes place between 120 and 160° C.

In some embodiments, the conversion is implemented over a time period between 1 min and 48 hours. In some embodiments, the conversion is implemented over a time period between 0.5 and 4 hours.

In some embodiments, subsequent to or at the same time during the conversion, at least one purification step of the mixture of compounds of Formulae Ia, Ib and/or Ic, obtained by the conversion, follows or is implemented, the ratio of the sum of the compounds of Formula Ia and Ib to the compound of Formula Ic (Ia+Ib)/Ic being increased to at least 10:1. In some embodiments, the ratio is increased to at least 100:1. In some embodiments, the ratio is increased to at least 1,000:1. In some embodiments, the compound of Formula Ic is substantially completely or completely removed. There is thereby understood by "substantially complete removal" a reduction in the content of compound Ic to concentrations in the 0/00 range.

In some embodiments, production of a mixture that only includes the compounds of Formulae Ia and Ib is hence made possible. In some embodiments, this mixture is a racemate, i.e. an equimolar mixture of compounds Ia and Ib which is termed racemic lactide.

In some embodiments, the previously mentioned purification step is thereby selected from the group consisting of filtration, washing, distillation, crystallization and/or recrystallization of the mixture of the compounds of Formula Ia, Ib and/or Ic, and also combinations of the mentioned purification steps. Combinations can thereby be implementation of the previously mentioned purification methods, following each other in succession or at the same time. For example, filtration or washing of the mixture obtained during the conversion are possible for this purpose, followed by a distillation or a crystallization; however, for example a distillation followed by a crystallization is likewise possible.

The crystallization and/or recrystallization can be implemented from the melt or from solvents. In some embodiments, the solvent may be selected from the group of alcohols, esters, ketones, hydrocarbons etc., e.g. acetone, isopropanol, ethylacetate, toluene and/or combinations hereof. In some embodiments, the crude obtained product from Ia, Ib and Ic is purified by recrystallization from the melt, Ia and Ib being crystallized out as pure product.

TABLE 2

Melting temperatures of the lactides

|  | L,L-lact. | D,D-lact. | M-lact. | L,L/D,D-lact. |
| --- | --- | --- | --- | --- |
| Tm ° C. | 97 | 97 | 54 | 129 |

After separating the melt that remains during the crystallization and contains compound Ic possibly in the mixture with Ia and/or Ib, the latter can be returned to the reaction stage. In this way, e.g. complete conversion of Ic can be transformed into an equimolar mixture of Ia and Ib.

In some embodiments, a substantially enantiomer-pure or enantiomer-pure compound of Formula IIa or IIb can be used according to variant 1).

In some embodiments, the method according to the invention relates to the production of an equimolar mixture of the two enantiomers of the dilactide of lactic acid, D,D-dilactide and L,L-dilactide, in which a) (−)-form L-(−)-lactic acid is converted with trioctylamine into trioctyl ammonium lactate, b) the trioctyl ammonium lactate is distilled in the presence of a catalyst, a fraction being obtained which is composed essentially of the two enantiomers of the dilactide of lactic acid, D,D-dilactide and L,L-dilactide and can still contain D,L-lactide, c) the above-mentioned fraction being mixed with acetone and hence recrystallized, and colorless crystals being obtained with a melting point of 112 to 119° C. which are composed substantially equimolarly or equimolarly of D,D-dilactide and L,L-dilactide.

According to some embodiments of the invention, the production of a racemate of L,L-dilactide and D,D-dilactide is hence made possible. The conversion (reaction with the catalyst) and the first purification step (distillation) thereby take place simultaneously.

Possibilities for use according to the invention of the mixture produced according to the method according to the invention are for example the subsequent (e.g. directly after the method according to the invention) production of amorphous polylactides and in particular the production of stereocomplex polylactic acid and/or stereoblock copolymers of lactic acid with stereoselective catalysts.

In some embodiments, the invention relates to a method for producing an equimolar mixture of D,D-dilactide and L,L-dilactide, the process for the production of these substances starting with L-(−)-lactic acid which is converted with trioctylamine into trioctyl ammonium lactate which is subjected to distillative resolution (in the sense of a condensation of two lactic acid units with racemization), a distillate being obtained which is recrystallized from acetone and thus the dilactide according to the invention is obtained.

It was now found that the dilactide mixture that includes in equal parts D,D-dilactide and L,L-dilactide can be produced simply if the distillate which is obtained from the thermolysis of the ammonium lactate is subjected to recrystallization. The thus obtained dilactide mixture has substantial advantages in the production of polymers from lactic acid which have improved physical properties.

In order to produce this dilactide, the process starts with L-lactic acid which is converted with trioctylamine into trioctyl ammonium lactate. In some embodiments, tri-n-octylamine is used as trioctylamine. Trioctyl ammonium lactate is thereby formed, which is subjected to distillative resolution (in the sense of a condensation of two lactic acid units with racemization). During the distillative resolution, a mixture that includes lactic acid and trioctylamine is obtained. A further fraction includes dilactide that is distilled over firstly to be water-white and then increasingly yellow. The distillative resolution (in the sense of a condensation of two lactic acid units with racemization) takes place in the presence of a catalyst. The fraction from the distillative resolution, which predominantly includes dilactide, is recrystallized after chilling. In some embodiments, acetone is used as solvent. Colorless crystals which have a melting point of 112° C. to 119° C. are thereby obtained.

The obtained crystals were subjected to analysis by gas chromatography using a chiral separation column. During the analysis, two equal area signal peaks were observed that could be assigned to D,D-dilactide and L,L-dilactide. The stereochemical configuration of the dilactides was confirmed by an enzymatic hydrolysis of the dilactides, in which a mixture composed with the same mass of lactic acid of respectively one stereochemical configuration was obtained. In the unpurified distillate, a further, significantly weaker signal which was assigned to the meso-lactide (dimer of D- and L-lactic acid) is observed during the hydrolysis in the process of the gas-chromatographic analysis.

In some embodiment, a method is described for producing an equimolar mixture of the two enantiomers of the dilactide of lactic acid, the one enantiomeric dilactide termed D,D-dilactide being formed from two (+)-form enantiomers of lactic acid and the other enantiomeric dilactide termed L,L-dilactide being formed from two (−)-form enantiomers of lactic acid, wherein trioctyl ammonium lactate is produced firstly from (−)-form L-(−)-lactic acid and trioctylamine, the thus obtained trioctyl ammonium lactate is subjected to distillative resolution (a mixture of trioctylamine and lactic acid being distilled over) and the distillative resolution of the trioctyl ammonium lactate is implemented in the presence of a catalyst, and a further fraction which is composed to a predominant proportion of the dilactide of lactic acid and which can still contain D,L-dilactide is obtained, and this fraction is mixed with acetone and hence recrystallized so that colorless crystals with a melting point of 112 to 119° C. which are composed equimolarly of D,D-dilactide and L,L-dilactide are obtained.

The formation of the enantiomer-similar dilactides from enantiomer-pure lactic acid as starting material can be explained in that the content of trioctylamine during the distillation effects a racemization of the lactic acid which then forms a racemic trioctyl ammonium lactate which after the distillative resolution, in some embodiments crystallizes to form enantiomer-like dilactide. The starting material had an enantiomer purity of approx. 1 percent by mass of D-lactic acid.

In some embodiments, a method is described in which a mixture is formed, which mixture is composed, in respectively equal parts, of 40 to 50 percent by mass of D,D-dilactide and L,L-dilactide and which contains as remaining component for example meso-lactide (D,L-dilactide). According to the production, the remaining constituent amount can also include oligolactides or further products of the distillative resolution.

In some embodiments, the distillative resolution of the trioctylammonium lactate is implemented in the presence of a catalyst. Organotin compounds are particularly suitable for this purpose. By way of example, dibutyltin oxide is used as catalyst in a quantity of 0.1 to 1 percent by mass, relative to the mixture in the distillation sump during the distillative resolution. According to the desired purity and yield of the dilactide, the distillative resolution is implemented in the presence of a distillation column. When using a distillation column, it is advantageous to implement the distillation in a vacuum (e.g. 20 mbar).

During the distillative resolution, a precursor that includes lactic acid and trioctylamine of an unknown composition is obtained. This corresponds to a constituent amount of 30 to 35 percent by mass of the starting quantity of trioctyl ammonium lactate. This proportion is dependent upon the evaporator temperature. Amine contents of 15 percent by mass (140° C.) to 25 percent by mass (165° C.) were measured in the distillate. Obviously, in addition to the lactic acid and amine, also certain constituent amounts of oligolactides are still contained in the distillate. The remaining constituent amount is distilled over as dilactide. In the distillation sump, approx. 2 to 3 percent by mass of a dark brown liquid remain.

In some embodiments, a dilactide of lactic acid is characterized in that it concerns a mixture which is composed respectively in equal parts of 50 percent by mass of D,D-dilactide and L,L-dilactide and which is produced with the method according to the invention. According to the production process, the mixture can also contain impurities. Therefore, a dilactide of lactic acid may include a mixture of D,D-dilactide and L,L-dilactide and further components, said mixture being produced with the method according to the invention.

The embodiment of the method according to the invention is explained by a general production diagram and experimental examples, these examples representing only typical embodiments.

General Production Diagram

In some embodiments, during the production of lactide, a racemization is effected and, in addition to the desired R-LA, M-LA is formed. The racemization takes place on the lactide molecule. The proton on the asymmetrical carbon atom is sensitive to weakly alkaline compounds and is removed in an equilibrium reaction. By replacing the proton, the stereogenic centre can be changed and a different steric configuration can be formed. This is shown below:

-continued

For direct production of rac-lactide, the process starts with L-, D- or D,L-lactic acid. After dewatering of the lactic acid, a tin compound is added as catalyst, as was already described, and also a weakly alkaline compound and then the distillation is started. Both an rac-lactide and a further compound which was identified as meso-lactide were found.

In some embodiments, the process may be represented by:

Diagram A: LAC→PLA→LA

LAC=lactic acid
PLA=polylactic acid
LA=lactide

In some embodiments, the process may be represented by:

Diagram A1

LAC = L-LAC, D-LAC, D,L-LAC-ester, mixtures
$P_{cat}$ = polymerization catalyst
$R_{cat}$ = polymerization catalyst As next step, a reaction with a PLA with a low molecular weight and the above-mentioned catalysts was implemented. Here also, an identical reaction product was obtained, i.e. a mixture of rac-lactide and meso-lactide, as shown below:

Diagram A2

PLA = PLLA, PDLA, PRLA, PMLA, mixtures, copolymers

Furthermore, a reaction analogous to L-, D- and meso-lactide was implemented. In each of these reactions, a lactide mixture was obtained as shown below:

Diagram A3

LA = L-LA, D-LA, M-LA mixtures of these lactides

This method for the production of rac-lactide in which all possible types of lactic acid or the derivatives thereof are used makes it possible to produce a monomer for the polymerisation of PLA without material loss since the meso-lactide can be used again after separation of rac-lactide during the racemization.

Figure 1:
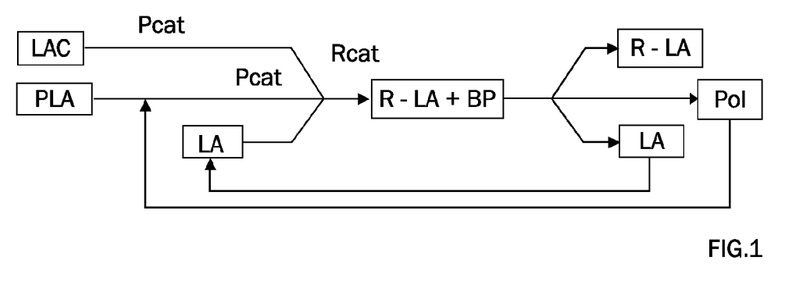
FIG. 1 illustrates a method in accordance with an embodiment of the invention.
Figure 2:
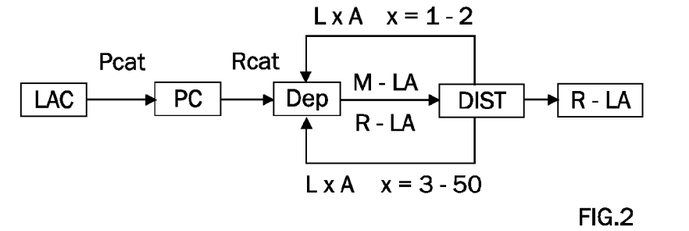
FIG. 2 illustrates a method in accordance with an embodiment of the invention.
Figure 3:
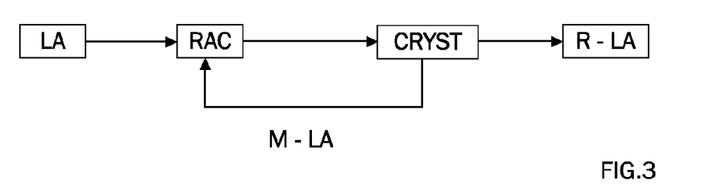
FIG. 3 illustrates a method in accordance with an embodiment of the invention.

FIGS. 1 through 3 illustrate methods in accordance with embodiments of the invention. In FIG. 1, PB represents byproducts while Pol represents the polymer. In FIG. 2, PC represents PLA with a low molecular weight, Dep represents depolymerization and DIST represents distillation. In FIG. 3, CRYST represents crystallization.

As shown in FIGS. 1-3, it is possible to produce sc-PLA or sbc-PLA via stereoselective catalysts, which have a higher thermostability without separate production possibilities being provided for optically pure L-lactide and D-lactide and the polymers PLLA and PDLA thereof which have been required to date to produce stereocomplexes.

Figure 4:
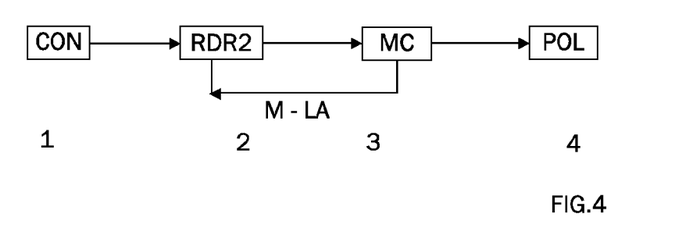
FIG. 4 illustrates a method in accordance with an embodiment of the invention.

Polymer-Production Chain:
Previously:

New:

FIG. 4 illustrates a polymer chain method in which CON represents the LAC concentrator, RDR2 represents a reactive distillation and racemization reactor, MC represents a melt crystallizer, and POL represents a polymerization reactor.

EXPERIMENTAL

Analysis Methods:
$^1$H-NMR NMR-spectra were recorded with a 500 MHz Varian-Inova spectrometer at a frequency of 499.85 MHz. The samples were measured in an approx. 5% $CDCl_3$ solution with tetramethylsilane as internal standard HPLC Knauer system with a Smartline 1000 pump and a Smartline 2500 UV-Detector. A Eurocel 03 column 5 μm 250×4.6 mm. Solvent hexane:ethanol=90:10 (v:v) 1 ml/min. Sample concentration 1-10 mg/ml.

GC Perkin-Elmer Clarus 500 with an FID; an FS-CW20M-CB-0.25 column (length=25 m, diameter=0.25 mm, film thickness=0.22 μm) inj. 200° C. temp.prog. 50-200° C., inj.vol.=1.0 μl, gas=nitrogen.

Example 1

In a mixing vessel, trioctylamine and L-lactic acid with an optical purity of 99% L-lactic acid was converted by heating to form trioctyl ammonium lactate. This was placed in a distillation vessel that was equipped with a reducing Liebig cooler and an Anschütz-Thiele distillation adaptor. Furthermore, 1 percent by mass (relative to lactic acid) dibutyltin oxide was placed as catalyst in the recipient vessel.

Heating to 250° C. then takes place. Firstly, two fractions at 140° C. and 165° C. distillation temperature were obtained, which, according to a gas chromatographical analysis, include 15 percent by mass (140° C.) and 25 percent by mass (165° C.) of amine. Thereafter, a water-white liquid was distilled over and became yellow-colored in the course of the distillation. The liquid was cooled and placed in acetone, out of which colorless crystals of melting point 112° C. to 119° C. were crystallized. The composition thereof was determined by GC analysis and hydrolytic resolution by enzymes as up to respectively 50 percent by mass of D,D-dilactide and L,L-dilactide of lactic acid.

Example 2

A further variant of the above-mentioned method according to the invention provides in particular to racemize substantially enantiomer-pure dilactide or meso-dilactide and also to convert mixtures of L-lactide and/or D-lactide and/or meso-lactide by racemization (variant 2).

It was found surprisingly that the above-indicated catalysts change pure meso-lactide or mixtures of meso-lactide and L,L-lactide in their composition. After purification and analysis, it was established that racemic lactide was obtained, consequently the catalyst had converted meso-lactide into racemic lactide.

Racemic lactide can be produced from racemic lactic acid by polycondensation and subsequent depolymerization. On the one hand, the large quantity of meso-lactide which is produced as by-product (40-60%) and the availability and the price of lactic acid racemate is thereby problematic.

The racemization of meso-lactide into racemic lactide offers a great chance of increasing the value of the meso-lactide since, with available stereoselective catalysts, the production of sc-PLA and/or sbc-PLA is possible. From an economic point of view, these products are very interesting materials since they have good thermal properties compared with PLLA.

Inspired by this knowledge, the inventors tested a large number of compounds for their catalytic activity in this reaction and surprisingly found that several classes of compounds showed an effect. The compounds were also tested for their activity for the reaction of L-lactide and D-lactide: racemization was also able to be established here.

Example 3

In a round flask with a distillation attachment, Liebig cooler and Anschütz-Thiele distillation adaptor, pure L-lactic acid 99% and trioctylamine were mixed. After the addition of 1% by weight of dibutyltin oxide (relative to the lactic acid), the mixture was heated to 250° C. and two fractions were collected, one at T<140° C. and one at T=140-165° C. By means of GC analysis, an amine content of 15 and 25% by weight was determined. The third fraction was a clear liquid from which colorless crystals were obtained. The melting point of the crystals was 112-119° C. and, by means of GC analysis and a hydrolysis with enzymes, a 50:50 mixture of D,D-lactide and L,L-lactide was established.

Example 4

A distillation structure was filled with 396.8 g L-LAC and 2.93 g KOH. After removing water by means of a vacuum, 0.506 g $SnOc_2$ was added; the temperature was increased from 150° C. to 240° C. and the pressure was lowered to 10 mbar. Three fractions which were collected in a temperature range of 100° C. to 150° C. contain the compounds. The total yield was 46% (L-LA:D-LA:M-LA=54:18:28).

Example 5

A distillation structure was filled with 253 g PLLA (Mn=750), 0.97 g Acima TW-30 ($SnOc_2$) and 2.53 g $K_2CO_3$. The temperature was increased to 210° C. and the pressure was lowered to 10 mbar. A fraction was collected in a temperature range of 140° C. to 148° C., an analysis producing a composition of 33% L-lactide, 30% D-lactide and 37% meso-lactide at a yield of 75% (variant 3).

Example 6

In a headspace jar, the lactide and the racemization catalyst were mixed and heated to 105° C. to 155° C. After 1 to 6 hours, the reaction was stopped by cooling the flask. The reaction product was analysed by $^1$H-NMR.

The precise reaction conditions and also educts and catalysts which are used are indicated in Tables 3 to 7.

TABLE 3

Racemization of meso-lactide

| Exp. No. | Temp ° C. | Time H | Cat. | Mol. Lac./Cat. | Mono-mer | % m-LACT* | % L,L/D,D-LACT* |
|---|---|---|---|---|---|---|---|
| 1 | 140 | 4 | $K_2CO_3$ | 824 | 82 | 37 | 63 |
| 2 | 140 | 6 | $K_2CO_3$ | 825 | 77 | 27 | 73 |
| 3 | 140 | 6 | TBA | 679 | 94 | 30 | 70 |
| 4 | 140 | 6 | DCHA | 693 | 95 | 34 | 66 |
| 5 | 140 | 24 | DCHA | 690 | 87 | 24 | 76 |
| 6 | 140 | 6 | DMAP | 709 | 84 | 27 | 73 |
| 7 | 140 | 24 | DMAP | 708 | 20 | 20 | 80 |
| 8 | 140 | 6 | TBP | 718 | 94 | 47 | 53 |
| 9 | 140 | 24 | TBP | 690 | 89 | 31 | 69 |

TBA = tributylamine
DCHA = dicyclohexylamine
DMAP = dimethylaminopyridine
TBP = tributylphosphine
*NMR-data; meso-lactide: 97% meso, 3% L

TABLE 4

Racemization of meso-lactide

| Exp. No. | Temp ° C. | Time H | Cat. | Mol. Lac./Cat. | Mono-mer | % m-LACT* | % L,L/D,D-LACT* |
|---|---|---|---|---|---|---|---|
| 1 | 125 | 1 | DCHA | 124 | § | 22 | 78 |
| 2 | 125 | 2 | DCHA | 124 | § | 19 | 81 |
| 3 | 125 | 3 | DCHA | 124 | § | 18 | 82 |
| 4 | 125 | 1 | TMPIP | 98 | § | 26 | 74 |
| 5 | 125 | 1 | PMPIP | 108 | § | 37 | 63 |
| 6 | 125 | 1 | EDiPA | 90 | § | 37 | 63 |
| 7 | 125 | 1 | TBA | 129 | § | 42 | 58 |

TABLE 4-continued

Racemization of meso-lactide

| Exp. No. | Temp °C. | Time H | Cat. | Mol. Lac./Cat. | Monomer | % m-LACT* | % L,L/D,D-LACT* |
|---|---|---|---|---|---|---|---|
| 8 | 125 | 1 | TOA | 245 | § | 37 | 63 |
| 9 | 125 | 1 | $K_2CO_3$ | 96 | & | 17 | 83 |

§ = no by-products
& = by-products
TMPIP = 2,2,6,6-tetramethylpiperidine
PMPIP = 1,2,2,6,6-pentamethylpiperidine
EDiPA = ethyldiisopropylamine
TBA = tributylamine
TOA = trioctylamine
*NMR-data; meso-lactide: 90% meso, 10% L

TABLE 5

Racemization of meso-lactide

| Exp. No. | Temp °C. | Time H | Cat. | Mol. Lac./Cat. | Monomer | % m-LACT* | % L,L/D,D-LACT* |
|---|---|---|---|---|---|---|---|
| 1 | 155 | 0.5 | DCHA | 124 | & | 25 | 75 |
| 2 | 155 | 1 | DCHA | 124 | § | 20 | 80 |
| 3 | 155 | 1 | TMPIP | 98 | § | 20 | 80 |
| 4 | 155 | 1 | PMPIP | 108 | § | 19 | 81 |
| 5 | 155 | 1 | EDiPA | 90 | § | 20 | 80 |
| 6 | 155 | 1 | TBA | 129 | § | 24 | 76 |
| 7 | 155 | 1 | KBenz | 111 | § | 16 | 84 |
| 8 | 155 | 1 | MgO | 28 | § | 43 | 57 |
| 9 | 155 | 1 | CaO | 39 | § | 36 | 64 |

§ = no by-products
& = by-products
KBenz = potassium benzoate
*NMR-data; meso-lactide: 90% meso, 10% L

TABLE 6

Racemization of L-lactide

| Exp. No. | Temp °C. | Time H | Cat. | Mol. Lac./Cat. | Monomer | % m-LACT* | % L,L/D,D-LACT* |
|---|---|---|---|---|---|---|---|
| 1 | 100 | 12 | DCHA | 20 | — | 18 | 82 |
| 2 | 130 | 20 | TOA | 245 | — | 24 | 76 |
| 3 | 130 | 1 | TOA | 10 | — | 18 | 82 |
| 4 | 130 | 1 | TEA | 5 | 30 | 0#) | 100#) |
| 5 | 130 | 1 | TOA | 15 | 89 | 0#) | 100#) |

)after with washing with $H_2O$
TEA = triethylamine
*NMR-data

TABLE 7

Racemization of meso-lactide

| Exp. No. | Temp °C. | Time H | Cat. | Mol. Lac./Cat. | Monomer | % m-LACT* | % L,L-LACT@ | % D,D-LACT@ |
|---|---|---|---|---|---|---|---|---|
| 1 | 140 | 2 | TBP | 694 | 98 | 79 | 13 | 8 |
| 2 | 140 | 6 | TBP | 718 | 94 | 42 | 30 | 28 |
| 3 | 140 | 24 | TBP | 690 | 89 | 31 | 35 | 34 |

TBP = tributylphosphine
*NMR-data; @ HPLC data; meso-lactide: 96% meso, 4% L

Example 7

Purification

Purification of the reaction products can be effected by means of fractionated distillation and/or crystallization. In some embodiments, crystallization can be implemented as liquid crystallization or as melt crystallization. In this way, only one separation of the meso-lactide is possible, L- and D-lactide (stereoisomers) cannot be separated by these physical methods. The experienced chemist will use ethyl acetate or toluene for the crystallization of lactide mixtures. Also alcohols, ketones etc. or mixtures hereof can serve for separation. In some embodiments, melt crystallization is used for the separation of lactides.

In a crystallization device, the melt of the lactide which has a temperature of 135° C. was slowly cooled and the solidified material (temperature 125° C.) was collected from the walls after the melt was removed. This process was repeated with the collected material until the desired purity was achieved. The melting temperature of the racemic lactide was 129° C. The remaining melt can be used again in the racemization reaction and the purification process can be repeated.

The invention claimed is:

1. A method for producing an equimolar mixture of D,D-dilactide and L,L-dilactide, the method comprising steps of:
    using trioctylamine to convert L-lactic acid into trioctyl ammonium lactate;
    distilling the trioctyl ammonium lactate in the presence of dibutyltin oxide $Bu_2SnO$;
    obtaining a fraction that includes D,D-dilactide and L,L-dilactide and can still contain D,L-lactide;
    mixing the fraction with acetone; and
    recrystallizing to obtain colorless crystals having a melting point of 112° C. to 119° C., the crystals being composed at least substantially equimolarly of D,D-dilactide and L,L-dilactide.

2. A method of producing a mixture of dilactides, the method comprising:
    reacting a starting material in the presence of one or more catalysts to produce a mixture of dilactides of Formulae Ia, Ib and Ic, Ia wherein the starting material is a substantially or completely stereoisomer-pure compound of Formula Ia, Ib or Ic or a mixture of two or three of the compounds, and R is a linear or branched aliphatic alkyl radical of 1 to 6 carbon atoms, wherein the one or more catalysts are selected from the group consisting of
  a) CaO, $K_2CO_3$, sodium lactate, potassium benzoate; oxides, hydroxides, carbonates, benzoates, lactates, octoates of Na, K, Ca, Fe, Ti, Zn or Sb, and/or
  b) primary, secondary and/or tertiary amines and/or aliphatic, aromatic N-heterocyclic compounds with 5-7 ring atoms or phosphines; primary, secondary and/or tertiary amines with 1 to 20 C-atoms; triethylamine, ethyldiisopropylamine, dibutylamine, tributylamine, trioctylamine, dicyclohexylamine, 4-(N,N-dimethyl)-aminopyridine, 2,2,6,6-tetramethylpiperidine, 1,2,2,6,6-pentamethylpiperidine and/or tributylphosphine;

and wherein the step of reacting a starting material is implemented at a temperature between about 80° C. and about 160° C.

3. The method according to claim 1, wherein the catalyst is added in a quantity of 0.1 to 1 percent by mass relative to the mixture in the distillation sump.

4. The method according to claim 1, wherein tri-n-octylamine is used to convert L-lactic acid into tri-n-octyl ammonium lactate.

5. The method according to claim 1, wherein the fraction obtained after distilling the trioctyl ammonium lactate in the presence of a catalyst is composed of 40 to 50 percent by mass of D,D-dilactide and L,L-dilactide which additionally may contain meso-lactide (D,L-dilactide) and/or oligolactides.

6. The method according to claim 1, wherein the distillation is implemented by means of a distillation column.

7. The method according to claim 1, wherein the distillation is implemented in a vacuum.

8. The method according to claim 2, wherein the catalyst is selected from the group consisting of the oxides, hydroxides, carbonates, benzoates, lactates, octoates of Na, K, Ca, Fe, Ti, Zn or Sb.

9. The method according to claim 2, wherein the catalyst is selected from the group consisting of CaO, $K_2CO_3$, sodium lactate, potassium benzoate.

10. The method according to claim 2, wherein the catalyst is selected from the group consisting of primary, secondary and/or tertiary amines and/or aliphatic, aromatic N-heterocyclic compounds with 5-7 ring atoms or phosphines.

11. The method according to claim 2, wherein the catalyst is selected from the group consisting of primary, secondary and/or tertiary amines with 1 to 20 C-atoms.

12. The method according to claim 2, wherein the catalyst is selected from the group consisting of triethylamine, ethyldiisopropylamine, dibutylamine, tributylamine, trioctylamine, dicyclohexylamine, 4-(N,N-dimethyl)-aminopyridine, 2,2,6,6-tetramethylpiperidine, 1,2,2,6,6-pentamethylpiperidine and/or tributylphosphine.

13. The method of claim 2, wherein the one or more catalyst, with respect to the starting material, is used in a weight ratio between 1:10 and 1:5,000.

14. The method of claim 2, wherein a molar ratio of the compounds of Formula Ia and Ib, obtained in the method, is between 1:2 and 2:1.

15. The method of claim 2, wherein a molar ratio of the sum of the compounds of Formula Ia and Ib, obtained in the method, to the compound of Formula Ic is between 10:1 and 1:1.

16. The method of claim 2, wherein the step of reacting a starting material occurs over a period of time of between about 0.5 and 4 hours.

17. The method of claim 2, further comprising a purification step, either during or after the reaction, in which a ratio of the sum of the compounds of Formula Ia and Ib to the compound of Formula Ic is increased to at least about 10:1.

18. The method of claim 17, wherein the purification step increases the ratio of the sum of the compounds of Formula Ia and Ib to the compound of Formula Ic to at least about 100:1.

19. The method of claim 17, wherein the purification step increases the ratio of the sum of the compounds of Formula Ia and Ib to the compound of Formula Ic to at least about 1000:1.

20. The method of claim 17, wherein the purification step comprises one or more of filtration, washing, distillation, crystallization and/or recrystallization.

21. The method of claim 20, wherein the crystallization and/or recrystallization is implemented from a melt or from a solvent.

22. The method of claim 17, wherein the solvent is selected from the group consisting of alcohols, esters, ketones, hydrocarbons, iso-propanol, ethylacetate, toluene and combinations thereof.

* * * * *